United States Patent [19]

(12) United States Patent
Fink

(10) Patent No.: US 7,071,169 B2
(45) Date of Patent: Jul. 4, 2006

(54) PYRANE DERIVATIVES AS BOTH ACE-AND NEP-INHIBITORS

(75) Inventor: Cynthia A Fink, Lebanon, NJ (US)

(73) Assignee: Novartis AG, Basel (CH)

( * ) Notice: Subject to any disclaimer, the term of this patent is extended or adjusted under 35 U.S.C. 154(b) by 239 days.

(21) Appl. No.: 10/487,742

(22) PCT Filed: Sep. 20, 2002

(86) PCT No.: PCT/EP02/10608

§ 371 (c)(1),
(2), (4) Date: Feb. 24, 2004

(87) PCT Pub. No.: WO03/027091

PCT Pub. Date: Apr. 3, 2003

(65) Prior Publication Data

US 2004/0266698 A1 Dec. 30, 2004

Related U.S. Application Data

(60) Provisional application No. 60/323,825, filed on Sep. 21, 2001.

(51) Int. Cl.
*A61K 38/00* (2006.01)
(52) U.S. Cl. ....................................................... 514/19
(58) Field of Classification Search .................... None
See application file for complete search history.

(56) References Cited

U.S. PATENT DOCUMENTS 5,506,244 A   4/1996  Fink ............................ 514/354
5,668,158 A   9/1997  Fink ............................ 514/354
2004/0235754 A1* 11/2004 Fink ............................. 514/19

FOREIGN PATENT DOCUMENTS

| EP | 0 468 339 A2 * | 1/1992 |
|---|---|---|
| EP | 0 468 339 B1 | 4/1997 |
| EP | 0 655 461 B1 | 6/2000 |
| WO | WO 99/55723 | 4/1999 |
| WO | WO 99/55726 * | 11/1999 |
| WO | WO 01/77095 A2 | 10/2001 |
| WO | WO 03/027091 A1 | 4/2004 |

OTHER PUBLICATIONS

Tsuda et al., Journal of Antibiotics Research Association, vol. 49, No. 9, (1996), Poststatin, a New Inhibitor of Endopeptidase V. Endopeptidase Inhibitory Activity of Poststatin Analogues.

* cited by examiner

*Primary Examiner*—Bruce R. Campell
*Assistant Examiner*—Thomas S. Heard
(74) *Attorney, Agent, or Firm*—Cynthia Zhang

(57) ABSTRACT

Compounds of the formula (I), wherein $R_1$, $R_1$–$R_7$ and alk have meaning as defined, pharmaceutical compositions thereof, and use thereof for the treatment and/or prevention of cardiovascular disorders responsive to ACE and NEP inhibition and/or ECE inhibition.

$$R_3S-\underset{\underset{R_5}{|}}{\overset{\overset{R_4}{|}}{C}}-\overset{O}{\overset{\|}{C}}-\overset{H}{\overset{|}{N}}-\underset{\underset{R_7}{|}}{\overset{\overset{R_6}{|}}{C}}-\overset{O}{\overset{\|}{C}}-\underset{}{N}-\underset{\underset{R}{|}}{\overset{\overset{alk-R_1}{|}}{CH}}-COOR_2.$$

(I)

19 Claims, No Drawings

PYRANE DERIVATIVES AS BOTH ACE-AND NEP-INHIBITORS

This application claims the benefit of U.S. provisional application No. 60/323,825, filed Sep. 21, 2001.

The present invention is directed to novel vasopeptidase inhibitors described below which are useful as dual inhibitors of both angiotensin converting enzyme (ACE) and neutral endopeptidase (NEP, EC 3.4.24.11). The compounds of the invention are particularly useful for the treatment and/or the prevention of conditions which are responsive to ACE and NEP inhibition. It can be shown that the compounds of the invention also inhibit endothelin converting enzyme (ECE) and are useful for the treatment and/or prevention of conditions which are responsive to ECE inhibition.

The present invention relates to the dual ACE and NEP inhibiting compounds of formula I

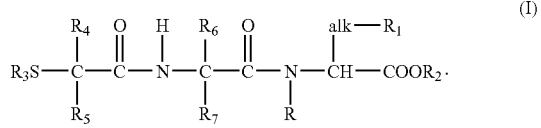

wherein
R represents hydrogen, lower alkyl, carbocyclic or heterocyclic aryl-lower alkyl or cycloalkyl-lower alkyl;
$R_1$ represents hydrogen, cycloalkyl, carbocyclic or heterocyclic aryl, or biaryl;
alk represents lower alkylene;
$R_3$ represents hydrogen or acyl;
$R_4$ represents oxacycloalkyl, (thia-, oxothia- or dioxothia)-cycloalkyl, azacycloalkyl, or oxacycloalkyl-, (thia-, oxothia- or dioxothia)-cycloalkyl- or azacycloalkyl-lower alkyl;
$R_5$ represents hydrogen or lower alkyl;
$R_6$ represents lower alkyl, carbocyclic or heterocyclic aryl, (carbocyclic or heterocyclic aryl)-lower alkyl, cycloalkyl, cycloalkyl-lower alkyl, biaryl or biaryl-lower alkyl;
$R_7$ represents lower alkyl, (carbocyclic or heterocyclic aryl)-lower alkyl, cycloalkyl-lower alkyl or biaryl-lower alkyl; or
$R_6$ and $R_7$, together with the carbon atom to which they are attached, represent 3- to 10-membered cycloalkylidene which may be substituted by lower alkyl or aryl-lower alkyl or may be fused to a saturated or unsaturated carbocyclic 5- to 7-membered ring; or 5- or 6-membered (oxacycloalkylidene, thiacycloalkylidene or azacycloalkylidene), each optionally substituted by lower alkyl or aryl-lower alkyl; or 2,2-norbonylidene;
$COOR_2$ represents carboxyl or carboxyl derivatized in form of a pharmaceutically acceptable ester;

disulfide derivatives derived from said compounds wherein $R_3$ is hydrogen; and pharmaceutically acceptable salts thereof.

The present invention is also directed to pharmaceutical compositions comprising said compounds; methods for preparation of said compounds; intermediates; and methods of treating disorders in mammals which are responsive to ACE and NEP inhibition and, optionally, ECE inhibition by administration of said compounds to mammals in need of such treatment.

Encompassed by the instant invention are also any prodrug derivatives of compounds of the invention having a free carboxyl, sulfhydryl or hydroxy group, said prodrug derivatives being convertible by solvolysis or under physiological conditions to be the free carboxyl, sulfhydryl and/or hydroxy compounds. Prodrug derivatives are, e.g., the esters of free carboxylic acids and S-acyl and O-acyl derivatives of thiols, alcohols or phenols, wherein acyl has meaning as defined herein.

Pharmaceutically acceptable esters are preferably prodrug ester derivatives, such being convertible by solvolysis or under physiological conditions to the free carboxylic acids of formula I.

Pharmaceutically acceptable prodrug esters are preferably, e.g., lower alkyl esters, aryl-lower alkyl esters, α-(lower alkanoyloxy)-lower alkyl esters such as the pivaloyloxymethyl ester, and α-(lower alkoxycarbonyl, morpholinocarbonyl, piperidinocarbonyl, pyrolidinocarbonyl or di-lower alkylaminocarbonyl)-lower alkyl esters.

Pharmaceutically acceptable salts are salts derived from pharmaceutically acceptable bases for any acidic compounds of the invention, e.g., those wherein $COOR_2$ represents carboxyl. Such are, e.g., alkali metal salts (e.g., sodium, potassium salts), alkaline earth metal salts (e.g., magnesium, calcium salts), amine salts (e.g., tromethamine salts).

Compounds of formula I, depending on the nature of substituents, possess two or more asymmetric carbon atoms. The resulting diastereomers and optical antipodes are encompassed by the instant invention. The preferred configuration is indicated in formula Ia

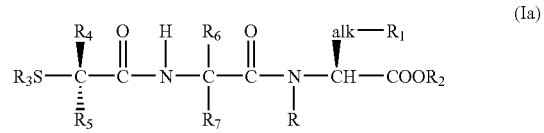

wherein asymmetric carbons carrying the substituents—alk-$R_1$ and $R_4$ typically have the S-configuration.

Preferred are the compounds of formula I and Ia wherein R and $R_5$ represent hydrogen; $R_1$ represents hydrogen, $C_5$- or $C_6$-cycloalkyl, carbocyclic or heterocyclic aryl, or biaryl; alk represents lower alkylene; $R_3$ represents hydrogen or acyl; $R_4$ represents oxacycloalkyl or oxacycloalkyl-lower alkyl; $R_6$ and $R_7$ represent lower alkyl; or $R_6$ and $R_7$, together with the carbon atom to which they are attached, represent 5- or 6-membered cycloalkylidene; $COOR_2$ represents carboxyl or carboxyl derivatized in form of a pharmaceutically acceptable ester; disulfide derivatives derived from said compounds wherein $R_3$ is hydrogen; and pharmaceutically acceptable salts thereof.

Further preferred are said compounds of formula I and Ia wherein R and $R_5$ represent hydrogen; $R_1$ represents carbocyclic or heterocyclic aryl, or biaryl; $R_3$ represents hydrogen or optionally substituted lower alkanoyl; $R_4$ represents tetrahydropyranyl or 4-tetrahydropyranylmethyl; $R_6$ and $R_7$ represent $C_1$–$C_4$-alkyl and are identical; alk represents methylene or ethylene; $COOR_2$ represents carboxyl, lower alkoxycarbonyl, (di-lower alkylaminocarbonyl)-lower alkoxycarbonyl or (morpholinocarbonyl, piperidinocarbonyl or pyrrolidinocarbonyl)-lower alkoxycarbonyl; and pharmaceutically acceptable salts thereof.

Particularly preferred are said compounds of formula I or Ia wherein R and $R_5$ represent hydrogen; $R_1$ represents carbocyclic aryl or heterocyclic aryl in which carbocyclic aryl represents phenyl or phenyl substituted by one or two of hydroxy, lower alkanoyloxy, lower alkyl, lower alkoxy, trifluoromethyl, trifluoromethoxy or halo and in which heterocyclic aryl represents indolyl; $R_3$ represents hydrogen or lower alkanoyl; $R_4$ represents 4-tetrahydropyranyl; $R_6$ and $R_7$ represent methyl; alk represents methylene or ethylene; and $COOR_2$ represents carboxyl or lower alkoxycarbonyl; and pharmaceutically acceptable salts thereof.

Also preferred are the above compounds of formula I or Ia wherein R and $R_5$ represent hydrogen; $R_1$ represents phenyl, flubrophenyl, methoxyphenyl, 2-thienyl-5-pyridyl, 4-biphenylyl, or 3-indolyl; $R_3$ represents hydrogen or lower alkanoyl; $R_4$ represents 4-tetrahydropyranyl; $R_6$ and $R_7$ represent methyl; alk represents methylene or ethylene; and $COOR_2$ represents carboxyl or lower alkoxycarbonyl; and pharmaceutically acceptable salts thereof.

In particular preferred are compounds of formula Ia wherein R and $R_5$ represent hydrogen; $R_1$ represents phenyl wich is unsubstituted or substituted by phenyl or $C_1$–$C_4$ alkoxy; or $R_1$ represents indolyl or pyridyl substituted by thienyl; $R_2$ represents hydrogen or $C_1$–$C_4$ alkyl; $R_3$ represents hydrogen or $C_2$–$C_5$ alkanoyl; $R_4$ represents tetrahydropyranyl or 4-tetrahydropyranylmethyl; $R_6$ and $R_7$ represent $C_1$–$C_4$ alkyl; or $R_6$ and $R_7$, together with the carbon atom to which they are attached, represent cyclopentylidene; alk represents $C_1$ to $C_2$ alkylene; or a pharmaceutically acceptable salt thereof.

The definitions as such or in combination as used herein, unless denoted otherwise, have the following meanings within the scope of the present invention.

Aryl represents carbocyclic or heterocyclic aryl, either monocyclic or bicyclic.

Monocyclic carbocyclic aryl represents optionally substituted phenyl, being preferably phenyl or phenyl substituted by one to three substitutents, such being advantageously lower alkyl, hydroxy, lower alkoxy, acyloxy, halogen, cyano, trifluoromethyl, trifluoromethoxy, amino, lower alkanoylamino, lower alkyl-(thio, sufinyl or sulfonyl), lower alkoxycarbonyl, mono- or di-lower alkylcarbamoyl, or mono- or di-lower alkylamino; or phenyl substituted by lower alkelenedioxy.

Bicyclic carbocyclic aryl represents 1- or 2-naphthyl or 1- or 2-naphthyl preferably substituted by lower alkyl, lower alkoxy or halogen.

Monocyclic heterocyclic aryl represents preferably thiazolyl, thienyl, furanyl, pyridyl, pyrimidinyl, oxazolyl, isoxazolyl, pyrrolyl, imidazolyl or oxadiazolyl, each being optionally substituted, e.g., by lower alkyl and the like.

Optionally substituted furanyl represents 2- or 3-furanyl or 2- or 3-furanyl preferably substituted by lower alkyl.

Optionally substituted pyridyl represents 2-, 3- or 4-pyridyl or 2-, 3- or 4-pyridyl preferably substituted by lower alkyl, halogen or cyano.

Optionally substituted thienyl represents 2- or 3-thienyl or 2- or 3- thienyl preferably substituted by lower alkyl.

Bicyclic heterocyclic aryl represents preferably indolyl or benzothiazolyl optionally substituted by hydroxy, lower alkyl, lower alkoxy or halogen, advantageously 3-indolyl or 2-benzothiazolyl.

Aryl as in aryl-lower alkyl is preferably phenyl or phenyl substituted by one or two of lower alkyl, lower alkoxy, hydroxy, lower alkanoyloxy, halogen, trifluoromethyl, cyano, lower alkanoylamino or lower alkoxycarbonyl; also, optionally substituted naphthyl.

Aryl-lower alkyl is advantageously benzyl or 1 - or 2-phenethyl optionally substituted on phenyl by one or two of lower alkyl, lower alkoxy, hydroxy, lower alkanoyloxy, halogen or trifluoromethyl.

The term "lower" referred to herein in connection with organic radicals or compounds respectively defines such with up to and including 7, preferably up to and including 4 and advantageously one or two carbon atoms. Such may be straight chain or branched.

Optionally substituted lower alkyl refers to lower alkyl or lower alkyl substituted by, e.g., halo, hydroxy, lower alkoxy, amino, (mono- or di-lower alkyl) amino, acylamino, 1-lower alkyl-piperazino, morpholino, piperidino, pyrrolidino and the like.

Lower alkylene refers to a straight or branched divalent carbon chain having preferably 1 to 4 carbon atoms, which may be substituted, e.g., by lower alkoxy, for example, —$CH_2$—, —$CH(CH_3)$—, —$CH_2CH_2$— and the like.

A lower alkyl group preferably contains 1–4 carbon atoms which may be straight chain or branched and represents, e.g., ethyl, propyl, butyl or advantageously methyl.

A lower alkoxy group preferably contains 1–4 carbon atoms which may be straight chain or branched and represents, e.g., methoxy, propoxy, isopropoxy or advantageously ethoxy.

Cycloalkyl represents a saturated cyclic hydrocarbon radical which preferably contains 5- to 7-ring carbons, preferably cyclopentyl or cyclohexyl.

Oxacycloalkyl represents preferably 5- to 7-membered oxacycloalkyl, e.g., tetrahydropyranyl, such as 4-tetrahydropyranyl.

Thiacycloalkyl represents preferably 5- to 7-membered thiacycloalkyl, e.g., tetrahydrothiopyranyl, such as 4-tetrahydrothiopyranyl.

Azacycloalkyl represents preferably 5- to 7-membered azacycloalkyl, e.g., pyrrolidinyl or piperidinyl in which the nitrogen may be substituted by lower alkyl or aryl-lower alkyl, such as 4-piperidinyl or 3-pyrrolidinyl optionally N-substituted by lower alkyl.

The term cycloalkyl-lower alkyl represents preferably (cyclopentyl or cyclohexyl)-methyl, 1- or 2-(cyclopentyl or cyclohexyl)ethyl, 1-, 2- or 3-(cyclopentyl or cyclohexyl) propyl, or 1-, 2-, 3- or 4-(cyclopentyl or cyclohexyl)-butyl. Similarly (oxacyclyl, thiacycloalkyl or azacycloalkyl)-lower alkyl.

A lower alkoxycarbonyl group preferably contains 1 to 4 carbon atoms in the alkoxy portion and represents, e.g., methoxycarbonyl, propoxycarbonyl, isopropoxycarbonyl or advantageously ethoxycarbonyl.

Cycloalkylidene is 3- to 10-membered, preferably 5- or 6-membered, and represents a cycloalkane linking group in which the two attached groups are attached to the same carbon of the cycloalkane ring, e.g., cyclopentylidene or cyclohexylidene.

5- or 6-membered oxacycloalkylidene represents a tetrahydrofuran or tetrahydropyran linking group, i.e., tetrahydrofuranylidene or tetrahydropyranylidene, in which the two attached groups are attached to the same carbon atom of the respective rings, e.g., at the 3- or 4-position thereof.

5- or 6-membered thiacycloalkylidene represents a tetrahydrothiophene or tetrahydrothiopyran linking group in which the two attached groups are attached to the same carbon atom of the respective rings, e.g., at the 3- or 4-position thereof.

5- or 6-membered azacycloalkylidene represents a pyrrolidine or piperidine linking group in which the two attached groups are attached to the same carbon atom of the respective rings, e.g., at the 3- or 4-position thereof, and the nitrogen may be substituted by lower alkyl, e.g., methyl, or by aryl-lower alkyl, e.g., benzyl.

Cycloalkylidene fused to a ring represents, e.g., benzofused cycloalkylidene, e.g., 1,1- or 2,2-tetralinylidene or 1,1- or 2,2-indanylidene.

Halogen (halo) preferably represents fluoro or chloro, but may also be bromo or iodo.

Acyl is derived from a carboxylic acid and represents preferably optionally substituted lower alkanoyl, carbocyclic aryl-lower alkanoyl, aroyl, lower alkoxycarbonyl or aryl-lower alkoxycarbonyl, advantageously optionally substituted lower alkanoyl, or aroyl Lower alkanoyl is preferably acetyl, propionyl, butyryl, or pivaloyl.

Optionally substituted lower alkanoyl, for example, represents lower alkanoyl or lower alkanoyl substituted by, e.g., lower alkoxycarbonyl, lower alkanoyloxy, lower alkanoylthio, lower alkoxy, lower alkylthio, hydroxy, di-lower alkylamino, lower alkanoylamino, morpholino, piperidino, pyrrolidino or 1-lower alkylpiperazino.

Aroyl is carbocyclic or heterocyclic aroyl, preferably monocyclic carbocyclic or monocyclic heterocyclic aroyl.

Monocyclic carbocyclic aroyl is preferably benzoyl or benzoyl substituted by lower alkyl, lower alkoxy, halogen or trifluoromethyl.

Monocyclic heterocyclic aroyl is preferably pyridylcarbonyl or thienylcarbonyl.

Acyloxy is preferably optionally substituted lower alkanoyloxy, lower alkoxycarbonyloxy, monocyclic carbocyclic aroyloxy or monocyclic heterocyclic aroyloxy, optionally substituted, e.g., as described for the groups involved.

Aryl-lower alkoxycarbonyl is preferably monocyclic carbocyclic-lower aloxycarbonyl, advantageously benzyloxycarbonyl.

Biaryl represents the grouping —Ar—Ar' in which Ar and Ar' independently represent monocyclic carbocyclic or heterocyclic aryl, namely (i) monocyclic carbocyclic aryl—monocyclic carbocyclic aryl (optionally substituted biphenylyl), (ii) monocyclic carbocyclic aryl—monocyclic heterocyclic aryl, (iii) monocyclic heterocyclic aryl—monocylic carbocyclic aryl, or (iv) monocyclic heterocyclic aryl—monocylic heterocyclic aryl. Monocyclic heterocyclic aryl in the groups Ar and/or Ar' in biaryl is preferably optionally substituted pyridyl (e.g., 3- or 4-pyridyl), thienyl (e.g., 2- or 3-thienyl), oxazolyl (e.g., 2-, 4- or 5-oxazolyl), thiazolyl (e.g., 2-, 4- or 5-thiazolyl), oxadizolyl (e.g., 3-[1,2,4] oxadiazolyl), furanyl (e.g., 2- or 3-furanyl), isoxazolyl (e.g., 4-isoxazolyl) or pyrimidinyl (e.g., 5-pyrimidinyl), in particular pyridyl and thienyl. Examples are 4-biphenylyl, optionally substituted on one or both phenyl rings by, e.g., lower alkyl, lower alkoxy, halogen or trifluoromethyl; also optionally substituted 5-phenyl-(2- or 3-thienyl), 5-phenyl-(2- or 3-furanyl), 2-phenyl-(4- or 5-oxazolyl), 2-phenyl-(4- or 5-thiazolyl), 5-phenyl-(3-[1,2,4]-oxadiazolyl) or 6-phenyl-3-pyridyl; also optionally substituted 4-(5-isoxazolyl)-phenyl, 4-(2-, 3- or 4-pyridyl)-phenyl, 4-(2- or 3-pyrolyl)-phenyl, 4-(2- or 3-furanyl)-phenyl, 4-(2- or 3-thienyl)-phenyl, or 4-(5-pyrimidinyl)-phenyl; also optionally substituted 6-(2- or 3-thienyl)-3-pyridyl, 6-(3-pyridyl)-3-pyridyl, 6-(2- or 3-furanyl)-3-pyridyl or 6-(2-thiazolyl)-3-pyridyl. Optional substituents on phenyl are as indicated for biphenylyl, and optional substituents on heterocyclic aryl groups are preferably lower alkyl, such as methyl.

The novel compounds of the invention are ACE inhibitors inhibiting the conversion of angiotensin I to the pressor substance angiotensin II and thus decrease blood pressure in mammals. Furthermore, compounds of the invention demonstrate inhibition of NEP and thus potentiate the cardiovascular (e.g., diuretic and natriuretic) effects of atrial natriuretic factors (ANF). The combined effect is beneficial for the treatment of cardiovascular disorders in mammals, in particular, hypertension, cardiac conditions such as congestive heart failure, and renal failure Including chronic and acute renal failure.

The above-cited properties are demonstrable in vitro and in vivo tests, using advantageously mammals, e.g., mice, rats, dogs, monkeys, or isolated organs, tissues and preparations thereof. Said compounds can be applied in vitro in the form of solutions, e.g., preferably aqueous solutions, and in vivo either enterally, parenterally, advantageously, orally or intravenously (i.v.), e.g., as a suspension or in aqueous solution. The dosage in vitro may range between about $10^{-6}$ molar and $10^{-9}$ molar concentrations. The dosage in vivo may range, depending on the route of administration, between about 0.01 and 50 mg/kg, advantageously between about 0.1 and 25 mg/kg.

In vitro testing is most appropriate for the free carboxylic acids of the invention. The test compound is dissolved in dimethyl sulfoxide, ethanol, or 0.25M sodium bicarbonate solution, and the solution is diluted with buffer to the desired concentration.

The in vitro inhibition of the ACE by the compounds of this invention can be demonstrated by a method analogous to that given in *Biochem. Pharmacol.*, Vol. 20, p.1637 (1971). The buffer for the ACE assay is 300 mM NaCl, 100 mM $KH_2PO_4$ (pH 8.3). The reaction is initiated by the addition of 100 μL of hippuryl-histidyl-leucine (2 mg/mL) to tubes containing enzyme and drug in a volume of 150 μL and tubes are incubated for 30 minutes at 37° C. The reaction is terminated by the addition of 0.75 mL 0.6N NaOH. 100 μL of freshly prepared o-phthalaldehyde solution (2 mg/mL in methanol) is added to the tubes, the contents are mixed and allowed to stand at room temperature. After 10 minutes, 100 μL of 6N HCl is added. The tubes are centrifuged and the supernatant optical density is read at 360 nm. The results are plotted against drug concentration to determine the $IC_{50}$, i.e., the drug concentration which gives half the activity of the control sample containing no drug.

Typically, the compounds of invention demonstrate an $IC_{50}$ in the range of about 0.1–50 nM for ACE inhibition.

Illustrative of the invention, the compound of Example 2g demonstrates an $IC_{50}$ of about 5.9 nM in the ACE in vitro assay.

Inhibition of ACE can be demonstrated in vivo on oral or i.v. administration by measuring inhibition of the angiotensin I induced pressor response in normotensive rats.

The in vivo test for i.v. administered compounds is performed with male, normotensive rats, which are anesthetized with sodium metofan. A femoral artery and femoral vein are cannulated respectively for direct blood pressure measurement on i.v. administration of angiotensin I and i.v. or p.o. administration of a compound of this invention. After the basal blood pressure is stabilized, pressor responses to 3 challenges of 300 ng/kg angiotensin I i.v., at 15 minute intervals, are obtained. Such pressure responses are usually again obtained at 15, 30, 60 and 90 minutes, and then every hour up to 6 hours after i.v. or p.o. administration of the compound to be tested, and compared with the initial responses. Any observed decrease of said pressor response is an indication of ACE inhibition.

Illustrative of the invention, the compound of Example 1f inhibits the angiotensin I induced pressor response for 4 hours at a dose of 10 mg/kg p.o. by 98%.

The in vitro inhibition of NEP (EC 3.4.24.11) can be determined as follows:

NEP 3.4.24.11 activity is determined by the hydrolysis of the substrate glutaryl-Ala-Ala-Phe-2-naphthylamide (GMP) using a modified procedure of Orlowski and Wilk (1981). The incubation mixture (total volume 125 µL) contains 4.2 µL of protein (rat kidney cortex membranes prepared by method of Maeda et al. (1983), 50 mM tris buffer, pH 7.4 at 25°0 C., 500 µM substrate (final concentration), and leucine aminopeptidase M (2.5 µg). The mixture is incubated for 10 minutes at 25° C., and 100 µL of fast garnet (250 µg fast garnet/mL of 10% Tween 20 in 1M sodium acetate pH 4.2) is added. Enzyme activity is measured spectrophotometrically at 540 nm. One unit of NEP 24.11 activity is defined as 1 nmol of 2-naphthylamine released per minute at 25° C. at pH 7.4. $IC_{50}$ values are determined, i.e., the concentration of test compound required for 50% inhibition of the release of 2-naphthylamine.

Typically, the compounds of the invention demonstrate an $IC_{50}$ in the range of about 0.1–50 nM for NEP inhibition.

Illustrative of the invention, the compound of Example 2g demonstrates an $IC_{50}$ of about 4.8 nM in the GAAP in vitro assay.

The antihypertensive activity can be determined, e.g., in the spontaneously hypertensive rat (SHR) and the desoxycorticosterone acetate (DOCA)-salt hypertensive rat, e.g., according to Trapani et al., *J. Cardiovasc. Pharmacol.*, Vol. 14, pp. 419–424 (1989).

Illustrative of the invention, the compound of example 1(f) reduces mean arterial pressure in conscious SHR by about 16 mm Hg at a dose of 11.6 mg/kg p.o.

The diuretic (saluretic) activity can be determined in standard diuretic screens, e.g., as described in "New Antihypertensive Drugs", Spectrum Publications, pp. 307–321 (1976), or by measuring the potentiation of atrial natriuretic factor-induced natriuresis and diuresis in the rat.

The in vitro inhibition of ECE can for example be determined as follows:

ECE is partially purified from porcine primary aortic endothelial cells by DE52 anion exchange column chromatography and its activity is quantified by RIA as described in *Anal. Biochem.*, Vol. 212, pp. 434–436 (1993). Alternatively, the native enzyme can be substituted by a recombinant form of ECE, as described, for example, in *Cell*, Vol. 78, pp. 473–485 (1994). Human ECE-1 has been described by several groups (see Schmidt et al., *FEBS Letters*, Vol. 356, pp. 238–243 (1994); Kaw et al., 4th Int. Conf. on Endothelin; April 23–25, London, UK (1995) C6; Valdenaire et al., *J. Biol. Chem.*, Vol. 270, pp. 29794–29798 (1995); Shimada et al., *Biochem. Biophys. Res. Commun.*, Vol. 207, pp. 807–812 (1995)). The ECE inhibition can be determined as described in *Biochem. Mol. Biol. Int.*, Vol. 31, No. 5, pp. 861–867 (1993), by RIA to measure ET-1 formed from big ET-1.

To assess the effect of an inhibitor on ECE-1 activity, 10 µg of protein is preincubated with the compound at a desired concentration for 20 minutes at room temperature in 50 mM TES, pH 7.0 and 0.005% Triton X-100 in a volume of 10 µL. Human big ET-1 (5 µL) is then added to a final concentration of 0.2 µM, and the reaction mixture is further incubated for 2 hours at 37° C. The reaction is stopped by adding 500 µL of RIA buffer containing 0.1% Triton X-100, 0.2% bovine serum albumin, and 0.02% $NaN_3$ in phosphate-buffered saline.

Diluted samples (200 pL) obtained from the above enzyme assay are incubated at 4° C. overnight with 25 µL each of $[^{125}I]$ET-1 (10,000 cpm/tube) and 1:20,000-fold diluted rabbit antibodies that recognize specifically the carboxyl terminal tryptophan of ET-1. Goat anti-rabbit antibodies coupled to magnetic beads (70 µg) are then added to each tube, and the reaction mixture is further incubated for 30 minutes at room temperature. The beads are pelleted using a magnetic rack. The supernatant is decanted, and the radioactivity in the pellet is counted in a gamma counter. Total and non-specific binding are measured in the absence of non-radioactive ET-1 and anti-ET antibodies, respectively. Under these conditions, ET-1 and big ET-1 displace $[^{125}I]$ET-1 binding to the antibodies with $IC_{50}$ values of 21±2 and 260,000±66,000 fmol (mean±SEM, n=3–5), respectively.

In order to determine the $IC_{50}$ value of an inhibitor, a concentration-response curve of each inhibitor is determined. An IBM-compatible version of ALLFIT program is used to fit data to a one-site model.

ECE inhibition can also be determined in vivo by measuring the inhibition of big ET-1-induced pressor response in the anesthesized or conscious rat, as described below. The effect of the inhibitors on the pressor response resulting from big ET-1 challenge is measured in Sprague-Dawley rats as described in *Biochem. Mol. Biol. Int.*, Vol. 31, No. 5, pp. 861–867 (1993). Results are expressed as percent inhibition of the big ET-1-induced pressor response as compared to vehicle.

Male Sprague-Dawley rats are anesthetized with Inactin (100 mg/kg i.p.) and instrumented with catheters in the femoral artery and vein to record mean arterial pressure (MAP) and administer compounds, respectively. A tracheostomy is performed and a cannula inserted into the trachea to ensure airway patency. The body temperature of the animals is maintained at 37±1° C. by means of a heating blanket. Following surgery, MAP is allowed to stabilize before interrupting autonomic neurotransmission with chlorisondamine (3 mg/kg i.v.). Rats are then treated with the test compound at 10 mg/kg i.v. or vehicle and challenged with big ET-1 (1 nmol/kg i.v.) 15 and 90 minutes later. Generally, the data are reported as the maximum increase in MAP produced by big ET-1 in animals treated with the test compound or vehicle.

ECE inhibition can also be determined in vivo by measuring the inhibition of the big ET-1 induced pressor response in conscious SHR, e.g., as described in *Biochem. Biophys. Res. Commun.*, Vol. 204, pp. 407–412 (1994).

The degree or lack of undesirable immunostimulatory potential of the compounds of the invention can be determined with the murine popliteal lymph node assay described in *Toxicology Letters*, Vols. 112/113, pp. 453–459 (2000).

Due to their inhibitory properties the compounds of the instant invention may be useful for the treatment and/or prevention of cardiovascular disorders, such as hypertension, renal failure (including edema and salt retention), e.g. chronic or acute renal failure, pulmonary edema, heart failure (including congestive heart failure), atherosclerosis, pain, depression, certain psychotic conditions, cognitive disorders, angina, premenstrual syndrome, Meniere's disease, hyperaldosteronism, hypercalciurea, ascites, glaucoma, asthma, gastrointestinal disorders such as diarrhea, irritable bowel syndrome and gastric hyperacidity, cerebral ischemia (stroke), subarachnoid hemorraghe, traumatic brain injury, cerebral vasospasm, arterial hypertrophy, restenosis, Raynaud's disease, myocardial infarction, obesity, prostate hyperplasia, migraine, diabetes mellitus, e.g. diabetic nephropathy, pre-eclampsia, transplant rejection such as in aorta or solid organ transplantation and erectile dysfunction.

The present invention furthermore relates to intermediates of compounds according to formula I, in particular to compounds of formular VI set forth herein below, wherein the variables alk, R, $R_1$, $R_2$, $R_4$, $R_5$, $R_6$, $R_7$ have the meanings given in each case for the corresponding variables of compounds of formula I or Ia, respectively.

The compounds of the invention, e.g., can be prepared
a) by condensing a compound of formula II

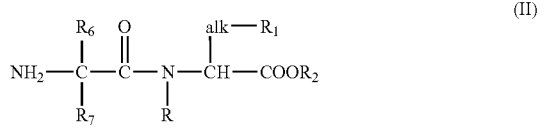

wherein the symbols alk, R, $R_1$, $R_6$ and $R_7$ have the meaning as defined above and $COOR_2$ represents esterified carboxyl, with a carboxylic acid of the formula III

or a reactive functional derivative thereof, wherein $R_4$ and $R_5$ have meaning as defined above; $R_3'$ represents hydrogen or a labile S-protecting group, e.g., acyl, t-butyl or optionally substituted benzyl; or
b) by condensing a compound of the formula IV

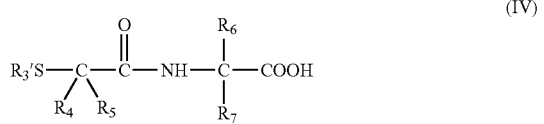

or a reactive functional derivative thereof wherein the symbols $R_3'$, $R_4$–$R_5$ and $R_6$–$R_7$ have meaning as defined above, with an amino acid ester of the formula V

wherein alk, R and $R_1$ have meaning as defined above and $COOR_2$ represents esterified carboxyl; or
c) by condensing under basic conditions a compound of the formula VI

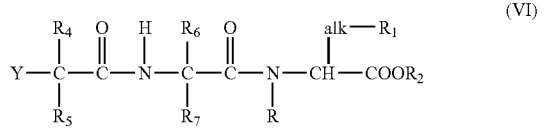

wherein the symbols R, $R_1$, $COOR_2$, $R_4$–$R_7$ and alk have meaning as defined above and Y represents a reactive esterified hydroxyl group (e.g., chloro or bromo) as a leaving group, with a compound of the formula

or a salt thereof, wherein $R_3$ represents a labile S-protecting group, e.g., acyl, t-butyl or optionally substituted benzyl; and converting a resulting product to a compound of formula I wherein $R_3$ is hydrogen;

and in above said process, if temporarily protecting any interfering reactive group(s), removing said protecting group(s), and then isolating the resulting compound of the invention; and, if desired, converting any resulting compound of the invention into another compound of the invention; and/or, if desired, converting a free carboxylic acid function into a pharmaceutically acceptable ester derivative, or converting a resulting ester into the free acid or into another ester derivative; and/or, if desired, converting a resulting free compound into a salt or a resulting salt into the free compound or into another salt, and/or, if desired, separating a mixture of isomers or racemates, and/or, if desired, resolving a racemate obtained into the optical antipodes.

In starting compounds and intermediates which are convened to the compounds of the invention in manner described herein, functional groups present, such as thiol, carboxyl, amino and hydroxy groups, are optionally protected by conventional protecting groups that are common in preparative organic chemistry. Protected thiol, carboxyl, amino and hydroxy groups are those that can be converted under mild conditions into free thiol, carboxyl, amino and hydroxy groups without other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (thiol, carboxyl, amino group, etc.), the structure and stability of the molecule of which the substituent is a part, and the reaction conditions.

Well-known protecting groups that meet these conditions and their introduction and removal are described, for example, in J. F. W. McOmie, "Protective Groups in Organic Chemistry", Plenum Press, London, N.Y. (1973); T. W. Greene and P. G. M. Wuts, "Protective Groups in Organic Synthesis", Wiley, N.Y. $3^{rd}$ Ed. (1999); and also in "The Peptides", Vol. 1, Schroeder and Luebke, Academic Press, London, N.Y. (1965).

The preparation of compounds of the invention according to process (a) involving the condensation of an amine of formula II with the acid of formula III or a functional reactive derivative thereof, is carried out by methodology well-known for peptide synthesis.

The condensation according to process (a) of an amino ester of formula II with a free carboxylic acid of formula III is carried out advantageously in the presence of a condensing agent such as dicyclohexylcarbodiimide, N-(3-dimethylaminopropyl)-N'-ethylcarbodiimide, hydroxybenzotriazole, 1-hydroxy-7-azabenzotriazole, chlorodimethoxytriazine, benzotriazol-1-yloxytris(dimethylamino)phosphonium hexafluorophosphate (BOP Reagent), or O-(7-azabenzotriazol-1-yl)-N,N,N',N'-tetramethyluronium hexafluorophosphate (HATU), either alone or in combination, and triethylamine or N-methylmorpholine, in an inert polar solvent, such as dimethylformamide or methylene chloride, preferably at room temperature.

The condensation of an amino ester of formula II with a reactive functional derivative of an acid of formula III in the form of an acid halide, advantageously an acid chloride, or mixed anhydride, is carried out in an inert solvent such as toluene or methylene chloride, advantageously in the presence of a base, e.g., an inorganic base such as potassium carbonate or an organic base such as triethylamine, N-methylmorpholine or pyridine, preferably at room temperature.

Reactive functional derivatives of carboxylic acids of formula III are preferably acid halides (e.g., the acid chloride) and mixed anhydrides, such as the pivaloyl or isobutyloxycarbohyl anhydride, or activated esters, such as benzotriazole, 7-azabenzotriazole or hexafluorophenyl ester.

The starting material of formula II can be prepared according to methods described herein and illustrated in the examples.

The preparation of a starting material of formula II involves the acylation of an ester of formula VIII

wherein alk, R and $R_1$ have meaning as defined hereinabove and $COOR_2$ represents esterified carboxyl (e.g., wherein $R_2$ is lower alkyl or benzyl) with an appropriately N-protected amino acid (or a reactive functional derivative) of formula IX

wherein $R_6$ and $R_7$ have meaning as defined hereinabove and $R_8$ is a labile amino protecting group, e.g., t-butoxycarbonyl, to obtain the corresponding N-protected compound of formula II.

The condensation of a compound of formula VII with a compound of formula IX is carried out by methodology well-known in peptide synthesis, e.g., as described above for the condensation of a compound of formula II with a compound of formula III. The N-protecting group is removed according to methods well-known in the art, e.g., the t-butoxycarbonyl is removed with anhydrous acid, such as trifluoroacetic acid or HCl.

The starting amino esters and acids of compounds of formula VIII and IX, respectively, are either known in the art, or if new, can be prepared according to methods well-known in the art, e.g., or illustrated herein. The amino acid esters of formula VIII are preferably the S-enantiomers.

The starting materials of formula III are known, or if new, may be prepared according to conventional methods. The starting materials are prepared, e.g., from the corresponding racemic or optically active α-amino acids, by conversion thereof to the α-bromo derivative followed by displacement thereof with inversion of configuration using the appropriate thiol derivative of formula VII, under basic conditions, for example, as illustrated in European Patent Application No. 524,553 published Jan. 27, 1993. S-debenzylation of the resulting final products is carried out by reductive cleavage, e.g., with Raney nickel in ethanol. S-deacylation is carried out by, e.g., base catalyzed hydrolysis with dilute aqueous sodium hydroxide. Cyclic starting materials of formula III can be prepared by treatment of the cyclic carboxylic acid (e.g., cyclopentanecarboxylic acid) with sulfur in the presence of a strong base, such as lithium diethylamide.

The preparation of the compounds of the invention according to process (b) involving the condensation of an acid of formula IV with an amino acid ester of formula V is carried out in a similar fashion to process (a). Similarly, the starting materials of formula IV are prepared by condensation of an acid of formula III with an ester corresponding to gem-disubstituted amino acids of formula IX (wherein $R_8$ is now hydrogen) under conditions similar to those described above, followed by removal of the carboxyl protecting group.

The preparation of the compounds of the invention according to process (c) involving the displacement of a leaving group Y in a compound of formula VI with a thiol derivative $R_3$'—SH as a salt thereof is carried out according to methods well-known in the art.

A reactive esterified hydroxyl group, represented by Y, is a hydroxyl group esterified by a strong inorganic or organic acid. Corresponding Y groups are in particular halo, for example, chloro, bromo or iodo, also sulfonyloxy groups, such as lower alkyl- or arylsulfonyloxy groups, for example (methane-, ethane-, benzene- or toluene-) sulfonyloxy groups, also the trifluoromethylsulfonyloxy group.

The displacement is carried out in an inert solvent, such as dimethylformamide or methylene chloride in the presence of a base, such as potassium carbonate, triethylamine, diisopropylethlamine, N-methylmorpholine and the like at room or elevated temperature. Using a salt of $R_3$'SH (e.g., potassium thioacetate), the reaction is carried out in the absence of a base, in an inert solvent, such as tetrahydrofuran or dimethylformamide.

Similarly, the starting materials of formula VI can be prepared by reacting the dipeptide derivative of formula II with an acid of the formula

wherein $R_4$ and $R_5$ and Y have meaning as defined above, under conditions described for process (a).

The compounds of formula X wherein Y is halo, such as the α-bromocarboxylic acids are known and are prepared, e.g., as described in International Application WO 99/55726 published Nov. 4, 1999.

Certain compounds of the invention and intermediates can be converted to each other according to general reactions well-known in the art.

The free mercaptans may be converted to the S-acyl derivatives by reaction with a reactive derivative of a carboxylic acid (corresponding to $R_3$ being acyl in formula I), such as an acid anhydride or said chloride, preferably in the presence of a base, such as triethylamine in an inert solvent, such as acetonitrile or methylene chloride.

Free alcohols and phenols can be converted to the corresponding acyl derivatives, e.g., by reaction with a corresponding acid chloride in the presence of a base, such as triethylamine.

The free mercaptans, wherein $R_3$ represents hydrogen, may be oxidized to the corresponding disulfides, e.g., by air oxidation or with the use of mild oxidizing agents, such as iodine in alcoholic solution. Conversely, disulfides may be reduced to the corresponding mercaptans, e.g., with reducing agents, such as sodium borohydride, zinc and acetic acid, or tributylphosphine.

Carboxylic acid esters may be prepared from a carboxylic acid by condensation with, e.g., the halide corresponding to $R_2$—OH, in the presence of a base, or with an excess of the alcohol in the presence of an acid catalyst, according to methods well-known in the art.

Carboxylic acid esters and S-acyl derivatives may be hydrolyzed, e.g., with aqueous alkali, such as alkali metal carbonates or hydroxides. S-acyl and ester groups can be selectively removed as illustrated herein.

Preferably, and wherever possible, the preferred isomers of the invention of formula la are prepared from pure enantiomers.

In case mixtures of stereoisomers (e.g., diasteromers) are obtained, these can be separated by known procedures, such as fractional crystallization and chromatography (e.g., thin layer, column, flash chromatography). Racemic free acids can be resolved into the optical antipodes by fractional crystallization of d- or l-(α-methylbenzylamine, cinchonidine, cinchonine, quinine, quinidine, dehydroabiethylamine, brucine or strychnine) salts and the like. Racemic products, if not diastereoisomers, can first be converted to diastereoisomers with optically active reagents, such as optically active alcohols to form esters, which can then be separated as described above, and, e.g., hydrolyzed to the individual enantiomer. Racemic products can also be resolved by chiral chromatography, e.g., high pressure liquid chromatography using a chiral absorbent; also by enzymatic resolution, e.g., of esters with alkalase.

The above-mentioned reactions are carried out according to standard methods, in the presence or absence of diluents, preferably such as are inert to the reagents and are solvents thereof, of catalysts, alkaline or acidic condensing or said other agents, respectively; and/or inert to the reagents and are solvents thereof, of catalysts, alkaline or acidic condensing or said other agents, respectively; and/or inert-atmospheres, at low temperatures, room temperature or elevated temperatures, preferably near the boiling point of the solvents used, at atmospheric or superatmospheric pressure.

The invention further includes any variant of said processes, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being preferred.

The present invention additionally relates to pharmaceutical compositions comprising the compounds of the invention and their pharmaceutically acceptable, non-toxic acid addition salts, either alone or in combination with one or more other pharmaceutically active agents. Such may be antihypertensive agents, antiatherosclerotic agents, cardiac agents, diuretic agents, cholesterol-lowering agents and the like. When used in combination with other therapeutic agents such can be administered separately or in a fixed combination.

Examples of therapeutic agents which can be used in combination are angiotensin II receptor antagonists, such as valsartan, losartan, candesartan, eprosartan, irbesartan, olmesartan, saprisartan, tasosartan and telmisartan; β-blockers, such as bisoprolol, propanolol, atenolol, sotalol and metoprolol; renin inhibitors, such as aliskiren, detikiren, terlakiren and zankiren; calcium channel blockers, such as amlodipine, verapamil, diltiazem, bepridil, felodipine, isradipine, lacidipine, nicardipine, nifedipine, niguldipine, niludipine, ryosidine, nimodipine and nisoldipine; aldosterone synthase inhibitors/aldosterone antagonists, such as eplerenone, (+)-fadrozole (WO 01/76574), spironolactone, anastrozole, exemesartane and canrenone; diuretics, such as bumetanide, ethacrynic acid, furosemide, torsemide, hydrochlorothiazide, indapamide, metazolone, amiloride, hydroflumethoazide, methylchlothiazide, metolazone, dichlorphenamide, triamterene, chlorothialidone and chlorothiazide; vasopressin receptor antagonists, such as OPC 21268, SR 49059, SR121463A, VPA985, WAY 140288, OPC31260 and YM087; cardiotonic drugs, such as enoximone and levosimendan; endothelin antagonists and ECE inhibitors, such as atrasentan, bosentan, darusentan, sitaxentan, tezosentan, BMS193884, J 104132, S 0139,TBC3711, YM 598 and compounds disclosed in WO 99/55726; anti-atherosclerotic agents, particularly cholesterol-lowering agents, such as bile acid sequestrants (e.g., cholestyramine and colestipol); cholesterol absorption inhibitors, such as ezetimibe; fibrates, such as fenofibrate and gemfibrozil; statin HMG CoA reductase Inhibitors, such as atorvastatin, cerivastatin, compactin, dalvastatin, dihydrocompactin, fluindostatin, fluvastatin, lovastatin, mevastatin, pravastatin, rivastatin, rosuvastatin, velostatin, simvastatin and pitavastatin; and nicotinic acid derivatives; thyromimetic agents, such as those disclosed in U.S. Pat. No. 5,569,674 and WO 00/58279; also antidiabetic agents, such as repaglinide, nateglinide, metformin, rosiglitazone, pioglitazone, darglitazone, englitazone, ciglitazone, AD 5075, AY 31637, BM 13.1246, DN 108, DRF 2189, KRP 297, MCC 555, T 174, YM 268, carbutamide, chloropropamide, glibenclamide, glibornuride, glibuzole, gliclazide, gliquidone, glisoxepid, glybuthiazole, glycopyramide, glyhexamide, glymidine, glypinamide, phenbutamide, tolazamide, tolbutamide, tolcyclamide, 1-butyl-3-meanylurea, glyburide, glipizide, glimepiride, isoleucin-thiazolidide, DPP728, LAF237, KAF 1229, NH622, glimepiride, mitiglinide, GLP-1(7–36), GLP-1(7–37), GLP-1(7–36)NH$_2$, GLN$^9$-GLP-1(7–37), D-GLN$^9$-GLP-1(7–37), acetyl LYS$^9$-GLP-1((7–37), LYS$^{18}$-GLP-1((7–37), GLP-1(7–37)OH, GLY$^8$-GLP-1(7–37), VAL$^8$-GLP-1(7–37), THR$^8$-GLP-1(7–37), Thr$^{16}$-Lys$^{16}$-Lys$^{18}$-GLP-1(7–37), MET$^8$-GLP-1(7–37), 4-imidazopropionyl-GLP-1, exedin-4, amylin, pramlintide, CCK 8, miglitol, voglibose, acarbose, insulin and the compounds disclosed in WO 99/20614, in particular DRF4158 which has the following structure:

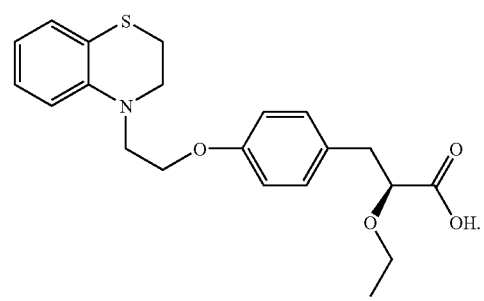

Also, the present invention relates to pharmaceutical compositions comprising the compounds of the present invention and their pharmaceutically acceptable, non-toxic acid addition salts, either alone or in combination with one or more other pharmaceutically active agents as named herein before for the treatment or prevention for conditions or disorders already disclosed herein.

Still further, the present invention relates to compounds of formula I, either alone or in combination with one or more pharmaceutically active agents as set forth herein, for the inhibition of ACE and NEP activity and, optionally, for the inhibition of ECE activity.

The present invention also relates to the use of the compounds or combinations of the invention for the preparation of pharmaceutical compositions and to pharmaceutical compositions for the treatment and/or prevention of conditions or disorders set forth herein, respectively.

Further, the present invention relates to a method of inhibiting angiotensin converting enzyme and neutral endopeptidase in mammals, including man, comprising administering to a mammal in need thereof an effective amount of a compound of the invention, either alone or in combination one or more other pharmaceutically active agents as indicated above.

The pharmaceutical compositions according the invention are those suitable for enteral, such as oral or rectal, transdermal and parenteral administration to mammals, including man, comprising an effective amount of a pharmacologically active compound of the invention or a pharmaceutically acceptable salt thereof, alone or in combination with one or more pharmaceutically acceptable carriers, as well as in combination with other therapeutic agents also useful for the treatment or prevention of conditions or disorders, as indicated above.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient, together with a) diluents, e.g., lactose, dextrose, sucrose, mannitol, sorbitol, cellulose and/or glycine; b) lubricants, e.g., silica, talcum, stearic acid, its magnesium or calcium salts and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desire, d) disintegrants, e.g., starches, agar, alginic acid or its sodium salt, or effervescent mixtures; and, if desired, absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

A unit dosage for a mammal of about 50 to 70 kg may contain between about 10 and 200 mg of the active ingredient. The dosage of active compound is dependent on the species of warm-blooded animal (mammal), the body weight, age and individual condition, and on the form of administration.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. Optical rotations (expressed in degrees) are measured at room temperature at 589 nM (D line of sodium) or other wave lengths as specified in the examples. The structure of the compounds are confirmed by standard analytical methods such as mass spectrum, elemental analysis, NMR, IR spectroscopy and the like.

The prefixes L, D, or R and S are used to indicate the absolute configuration at an asymmetric center.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active agents and, based on these references, likewise enabled to manufacture and test the pharmaceutical indications and properties in standard test models, both in vitro and in vivo.

The corresponding active ingredients or pharmaceutically active salts thereof may also be used in form of a solvate, such as a hydrate, or including other solvents used for crystallization.

EXAMPLE 1

(a) N-[1-[(S)-2-Acetylthio-2-(4-tetrahydropyranyl) acetylamino]-cyclopentanecarbonyl]-L-homophenylalanine ethyl ester

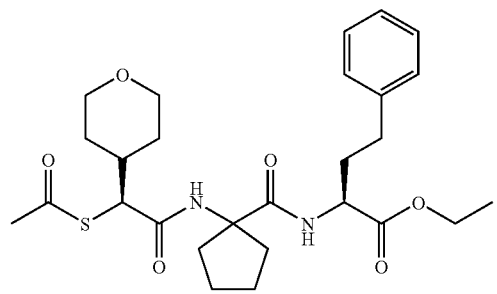

A mixture of potassium thioacetate (1.66 g, 14.6 mmol) and N-[1-[(R)-2-bromo-2-(4-tetrahydropyranyl)acetylamino]-cyclopentanecarbonyl]-L-homophenylalanine ethyl ester (1.84 g, 3.52 mmol) in 50 mL of tetrahydrofuran is stirred at room temperature for 4 hours. The mixture is diluted with ethyl acetate, washed with water, with saturated sodium bicarbonate solution, with brine and then dried over magnesium sulfate. The mixture is filtered and concentrated to dryness in vacuo. The residual oil is chromatographed on silica gel with hexane:ethyl acetate (50:50) to yield the title compound, m.p. 107–111° C.; [α]$_D$–56.27° (c=0.994, methanol).

The starting material is prepared as follows:

A solution of sodium nitrite (4.71 g, 68.3 mmol) in 35 mL of water is added dropwise to a chilled (0° C.) solution of (D)-α-(4-tetrahydropyranyl)-glycine (*J. Am. Chem. Soc.*, Vol. 117, pp. 9375–9376 (1995) (7.05 g, 44.3 mmol) and 48% HBr (aq) (70 mL) in 35 mL of water. Upon completion of the addition, the mixture is allowed to warm to room temperature, stirred at room temperature for 3 hours. The mixture is extracted with ethyl acetate; the organic layer is washed sequentially with water, 5% aqueous sodium thiosulfate, and brine, then dried over anhydrous magnesium sulfate. The mixture is filtered and concentrated in vacuo to yield (D)-α-bromo-α-(4-tetrahydropyranyl)-acetic acid as a solid.

The other intermediate is prepared as follows:

Hydrogen chloride gas is bubbled through a solution of (L)-homophenylalanine (5.13 g, 28.7 mmol) in 100 mL of ethanol for 5 minutes. The mixture is stirred at room temperature for 16 hours. The mixture is concentrated in vacuo to yield L-homophenylalanine ethyl ester hydrochloride as a white solid.

A mixture of (L)-homophenylalanine ethyl ester hydrochloride (6.87 g, 28.3 mmol), N-CBZ-cycloleucine (7.69 g, 29.2 mmol), 1-(3-diethylaminopropyl)-3-ethylcarbodiimide hydrochloride (5.44 g, 28.5 mmol), 1-hydroxybenzotriazole (3.96 g, 29.3 mmol) and triethylamine (2.90 mL, 28.7 mmol) in 150 mL of methylene chloride is stirred at room temperature for 16 hours. The mixture is concentrated in vacuo, the residue is taken up in ethyl acetate, the solution is washed with water, 1N HCl (aq), saturated sodium bicarbonate solution and brine, and then dried over magnesium sulfate. The mixture is filtered and concentrated in vacuo to yield N-(1-CBZ-aminocyclopentanecarbonyl)-(L)-homophenylalanine ethyl ester as a white solid; MS: M+1=453.

A solution of N-(1-CBZ-aminocyclopentanecarbonyl)-(L)-homophenylalanine (4.85 g, 10.7 mmol) in 150 mL of ethanol is hydrogenated in the presence of 10% palladium on carbon (0.5 g) at 45 psi of hydrogen pressure in a Parr bottle for 3 hours. The mixture is filtered through a pad of celite and concentrated in vacuo to give N-(1-aminocyclopentanecarbonyl)-(L)-homophenylalanine ethyl ester; MS: M+1=319.

A mixture of N-(1-aminocyclopentanecarbonyl)-(L)-homophenylalanine ethyl ester (3.62 g, 11.4 mmol), (D)-α-bromo-α-(4-tetrahydropyranyl)acetic acid (2.37 g, 10.7 mmol),1-(3-diethylaminopropyl)-3-ethylcarbodiimide hydrochloride (2.07 g, 0.8 mmol) and 1-hydroxy-7-azabenzotriazole (1.49 g, 11.0 mmol) in methylene chloride (100 mL) is stirred at room temperature for 16 hours. The mixture is evaporated to dryness in vacuo, the residue is taken up in ethyl acetate, the ethyl acetate solution is washed sequentially with water, 1N HCl (aq), saturated sodium bicarbonate solution and brine, then dried over anhydrous magnesium sulfate, and evaporated to dryness in vacuo. The resulting solid is chromatographed on silica gel with hexane and ethyl acetate (50:50) to yield N-[1-[(R)-2-bromo-2-(4-tetrahydropyranyl)acetylamino] cyclopentanecarbonyl]-(L)-homophenylalanine ethyl ester; MS: M+1=522.

Similarly prepared are:

(b) N-[1-[(S)-2-acetylthio-2-(4-tetrahydropyranyl)-acetylamino]-cyclopentanecarbonyl]-(L)-tryptophan ethyl ester; m.p. 67–77° C.; [α]$_D$–49.13° (c 1.079, DMSO).

(c) N-[1-[(S)-2-acetylthio-2-(4-tetrahydropyranyl)-acetylamino]-cyclopentanecarbonyl]-4-methoxyphenylalanine ethyl ester, m.p. 125–126° C.

(d) N-[1-[2-acetylthio-3-(4-tetrahydropyranyl)-propionylamino]-cyclopentanecarbonyl-(L)-homophenylalanine ethyl ester; m.p. 33–38° C.

(e) N-[2-[(S)-2-acetylthio-2-(4-tetrahydropyranyl) -acetylamino]-2-methylpropionyl]-(L)-homophenylalanine ethyl ester; m.p. 83–85° C.; [α]$_D$–45.48° (c 1.0, methanol); using BOC-A-methylalanine instead of CBZ-cycloleucine.

(f) N-[2-[(S)-2-acetylthio-2-(4-tetrahydropyranyl)-acetylamino]-2-methylpropionyl]-(L)-4-methoxyphenylalanine ethyl ester, m.p. 39–42° C.; [α]$_D$–44.3° (c 1.05, methanol).

(g) N-[2-[(S)-2-acetylthio-2-(4-tetrahydropyranyl)-acetylamino]-2-methylpropionyl]-(L)-4-biphenylalanine ethyl ester; m.p. 121–122° C.

(h) N-[2-[(S)-2-acetylthio-2-(4-tetrahydropyranyl)-acetylamino]-2-methylpropionyl]-(L)-[2-(2-thienyl)-5-pyridyl]-alanine n-butyl ester; m.p. 55–60° C.

(i) N-[1-[2-acetylthio-3-(4-tetrahydropyranyl)-propionylamino]-cyclopentanecarbonyl]-(L)-homopheny ethyl ester; m.p. 33–38° C.

(j) N-[1-[2-[(S)-2-acetylthio-2-(4-tetrahydropyranyl)-acetylamino]-2-methylpropionyl-(L)-tryptophan ethyl ester; m.p. 55–63° C.

EXAMPLE 2

(a) N-[1-[(S)-2-Mercapto-2-(4-tetrahydropyranyl)-acetyamino]-cyclopentanecarbonyl]-L-tryptophan

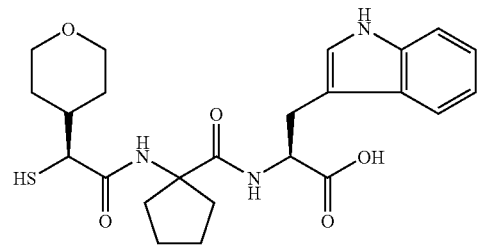

Under an argon atmosphere, a solution of N-[1 -[(S)-2-acetylthio-2-(4-tetrahydropyranyl)-acetylamino]-cyclopentanecarbonyl]-L-tryptophan (0.54 g, 1.0 mmol) in MeOH (5.0 mL) is treated with 1N NaOH (5.0 mL) and stirred at room temperature for 3 hours. The solution is acidified with 1 N HCl and concentrated in vacuo to remove most of the MeOH. The aqueous residue is extracted into EtOAc (3×5.0 mL) and the extracts are combined and washed with water (5.0 mL) and brine solution (5.0 mL). The solution is dried over Na$_2$SO$_4$, filtered and concentrated in vacuo. The product is crystallized from t-butyl methyl ether-hexane to yield to the title compound; m.p. 212–215° C.; [α]$_D$–6.580 (c 1.026, DMSO).

Similarly prepared are:

(b) N-[1-[(S)-2-mercapto-2-(4-tetrahydropyranyl)-acetylamino]-cyclopentanecarbonyl]-(L)-homophenylalanine; m.p. 193–195° C.; [α]$_D$–23.330 (c 1.05, methanol).

(c) N-[2-[(S)-2-mercapto-2-(4-tetrahydropyranyl)-acetylamino]-2-methylpropionyl]-(L)-homophenylalanine; m.p. 194–195° C.; [α]$_D$–8.2° (c 0.3, methanol).

(d) N-[2-[(S)-2-mercapto-2-(4-tetrahydropyranyl)-acetylamino]-2-methylpropionyl]-(L)-[2-(2-thienyl)-5-pyridyl]alanine; m.p. 192–193° C.

(e) N-[2-[(S)-2-mercapto-2-(4-tetrahydropyranyl)-acetylamino]-2-methylpropionyl]-(L)-biphenylalanine; m.p. 199–200° C.

(f) N-[1-[(S)-2-mercapto-2-(4-tetrahydropyranyl)-acetylamino]-cyclopentanecarbonyl]-(L)-4-methoxyphenylalanine; m.p. 220–221° C.

(g) N-[2-[(S)-2-mercapto-2-(4-tetrahydropyranyl)-acetylamino]-2-methylpropionyl]-(L)-4-methoxyphenylalanine; m.p. 182–183° C.

(h) N-[1-[(S)-2-mercapto-3-(4-tetrahydropyranyl)-propionylamino]-cyclopentanecarbonyl]-(L)-homophenylalanine; m.p. 145–147° C.

(i) N-[2-[(S)-2-mercapto-2-(4-tetrahydropyranyl)-acetylamino]-2-methylpropionyl]-(L)-tryptophan; m.p. 195–201° C.

EXAMPLE 3

(a) N-[2-[(S)-2-Mercapto-2-(4-tetrahydropyranyl)-acetylamino]-2-methylpropionyl]-L-homophenylalanine ethyl ester

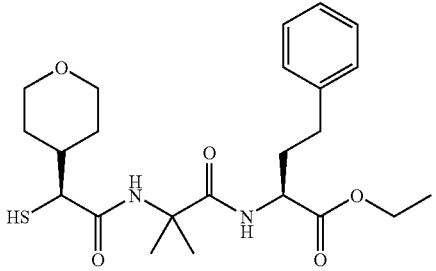

Under an argon atmosphere, the compound of example 1 (e) (0.49 g, 1.0 mmol) is dissolved in absolute ethanol (5 mL) and the solution is treated with 1 N NaOH (1.0 mL, 1.0 mmol). The mixture is stirred at room temperature for 4 hours and then treated with 1N HCl to pH 3. The mixture is evaporated to remove most of the ethanol and the product is extracted with ethyl acetate. The ethyl acetate extract is washed with water and then brine. The solution is then dried over sodium sulfate and evaporated to dryness. The product is triturated in methyl-t-butyl ether and hexane, then collected by filtration to give title compound; m.p. 157–158° C.; [α]$_D$–21.93° (c.0.$^{66}$, methanol).

Similarly prepared are:

(b) N-[2-[(S)-2-mercapto-2-(4-tetrahydropyranyl)-acetylamino]-2-methylpropionyl]-(L)-tryptophan ethyl ester; m.p. 138–145° C.; [α]$_D$–34.31° (c 1.057, DMSO).

(c) N-[1-[(S)-2-mercapto-2-(4-tetrahydropyranyl)-acetylamino]-cyclopentanecarbonyl]-(L)-tryptophan ethyl ester; m.p. 186–190° C.; [α]$_D$–25.72° (c 1.01, DMSO).

(d) N-[1-[2-mercapto-2-(4-tetrahydropyranyl)-propionylamino]-cyclopentanecarbonyl]-(L)-homophenylalanine ethyl ester; m.p. 92–94° C.; [α]$_D$–9.28° (c 1.14, methanol).

What is claimed is:

1. A compound of the formula

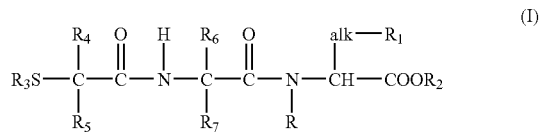

(I)

wherein

R represents hydrogen, lower alkyl, carbocyclic or heterocyclic aryl-lower alkyl or cycloalkyl-lower alkyl;

$R_1$ represents hydrogen, cycloalkyl, carbocyclic or heterocyclic aryl, or biaryl;

alk represents lower alkylene;

$R_3$ represents hydrogen or acyl;

$R_4$ represents oxacycloalkyl, (thia-, oxothia- or dioxothia)-cycloalkyl, azacycloalkyl, or oxacycloalkyl-, (thia-, oxothia- or dioxothia)-cycloalkyl- or azacycloalkyl-lower alkyl;

$R_5$ represents hydrogen or lower alkyl;

$R_6$ represents lower alkyl, carbocyclic or heterocyclic aryl, (carbocyclic or heterocyclic aryl)-lower alkyl, cycloalkyl, cycloalkyl-lower alkyl, biaryl or biaryl-lower alkyl;

$R_7$ represents lower alkyl, (carbocyclic or heterocyclic aryl)-lower alkyl, cycloalkyl-lower alkyl or biaryl-lower alkyl; or $R_6$ and $R_7$, together with the carbon atom to which they are attached, represent 3- to 10-membered cycloalkylidene which may be substituted by lower alkyl or aryl-lower alkyl or may be fused to a saturated or unsaturated carbocyclic 5- to 7-membered ring; or 5- or 6-membered (oxacycloalkylidene, thiacycloalkylidene or azacycloalkylidene), each optionally substituted by lower alkyl or aryl-lower alkyl; or 2,2-norbonylidene;

$COOR_2$ represents carboxyl or carboxyl derivatized in form of a pharmaceutically acceptable ester;

a disulfide derivative derived from a said compound wherein $R_3$ is hydrogen; or a pharmaceutically acceptable salt thereof.

2. A compound according to claim 1 of the formula

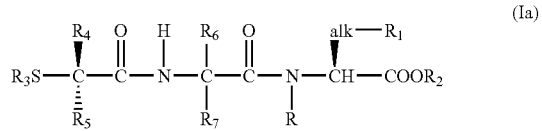

(Ia)

wherein asymmetric carbons carrying the substituents—alk-$R_1$ and $R_4$ typically have the S-configuration, or a disulfide derivative derived from a said compound wherein $R_3$ is hydrogen; or a pharmaceutically acceptable salt thereof.

3. A compound according to claim 1 of formula I wherein R and $R_5$ represent hydrogen; $R_1$ represents hydrogen, $C_5$- or $C_6$-cycloalkyl, carbocyclic or heterocyclic aryl, or biaryl; alk represents lower alkylene; $R_3$ represents hydrogen or acyl; $R_4$ represents oxacycloalkyl or oxacycloalkyl-lower alkyl; $R_6$ and $R_7$ represent lower alkyl; or $R_6$ and $R_7$, together with the carbon atom to which they are attached, represent 5- or 6-membered cycloalkylidene; $COOR_2$ represents carboxyl or carboxyl derivatized in form of a pharmaceutically acceptable ester; a disulfide derivative derived from a said compound wherein $R_3$ is hydrogen; or a pharmaceutically acceptable salt thereof.

4. A compound according to claim 2 of formula Ia wherein R and $R_5$ represent hydrogen; $R_1$ represents hydrogen, $C_5$- or $C_6$-cycloalkyl, carbocyclic or heterocyclic aryl, or biaryl; alk represents lower alkylene; $R_3$ represents hydrogen or acyl; $R_4$ represents oxacycloalkyl or oxacycloalkyl-lower alkyl; $R_6$ and $R_7$ represent lower alkyl; or $R_6$ and $R_7$, together with the carbon atom to which they are attached, represent 5- or 6-membered cycloalkylidene; $COOR_2$ represents carboxyl or carboxyl derivatized in form of a pharmaceutically acceptable ester; a disulfide derivative derived from a said compound wherein $R_3$ is hydrogen; or a pharmaceutically acceptable salt thereof.

5. A compound according to claim 1 of formula I wherein R and $R_5$ represent hydrogen; $R_1$ represents carbocyclic or heterocyclic aryl, or biaryl; $R_3$ represents hydrogen or optionally substituted lower alkanoyl; $R_4$ represents tetrahydropyranyl or 4-tetrahydropyranylmethyl; $R_6$ and $R_7$ represent $C_1$–$C_4$-alkyl and are identical; alk represents methylene or ethylene; $COOR_2$ represents carboxyl, lower alkoxycarbonyl, (di-lower alkylaminocarbonyl)-lower alkoxycarbonyl or (morpholinocarbonyl, piperidinocarbonyl or pyrrolidinocarbonyl)-lower alkoxycarbonyl; or a pharmaceutically acceptable salt thereof.

6. A compound according to claim 2 of formula Ia wherein R and $R_5$ represent hydrogen; $R_1$ represents carbocyclic or heterocyclic aryl, or biaryl; $R_3$ represents hydrogen or optionally substituted lower alkanoyl; $R_4$ represents tetrahydropyranyl or 4-tetrahydropyranylmethyl; $R_6$ and $R_7$ represent $C_1$–$C_4$-alkyl and are identical; alk represents methylene or ethylene; $COOR_2$ represents carboxyl, lower alkoxycarbonyl, (di-lower alkylaminocarbonyl)-lower alkoxycarbonyl or (morpholinocarbonyl, piperidinocarbonyl or pyrrolidinocarbonyl)-lower alkoxycarbonyl; or a pharmaceutically acceptable salt thereof.

7. A compound according to claim 1 of formula I wherein R and $R_5$ represent hydrogen; $R_1$ represents carbocyclic aryl or heterocyclic aryl in which carbocyclic aryl represents phenyl or phenyl substituted by one or two of hydroxy, lower alkanoyloxy, lower alkyl, lower alkoxy, trifluoromethyl, trifluoromethoxy or halo, and in which heterocyclic aryl represents indolyl; $R_3$ represents hydrogen or lower alkanoyl; $R_4$ represents 4-tetrahydropyranyl; $R_6$ and $R_7$ represent methyl; alk represents methylene or ethylene; and $COOR_2$ represents carboxyl or lower alkoxycarbonyl; or a pharmaceutically acceptable salt thereof.

8. A compound according to claim 2 of formula Ia wherein R and $R_5$ represent hydrogen; $R_1$ represents carbocyclic aryl or heterocyclic aryl in which carbocyclic aryl represents phenyl or phenyl substituted by one or two of hydroxy, lower alkanoyloxy, lower alkyl, lower alkoxy, trifluoromethyl, trifluoromethoxy or halo, and in which heterocyclic aryl represents indolyl; $R_3$ represents hydrogen or lower alkanoyl; $R_4$ represents 4-tetrahydropyranyl; $R_6$ and $R_7$ represent methyl; alk represents methylene or ethylene; and $COOR_2$ represents carboxyl or lower alkoxycarbonyl; or a pharmaceutically acceptable salt thereof.

9. A compound according to claim 1 of formula I wherein R and $R_5$ represent hydrogen; $R_1$ represents phenyl, fluorophenyl, methoxyphenyl, 4-biphenylyl, 2-thienyl-5-pyridyl, or 3-indolyl; $R_3$ represents hydrogen or lower alkanoyl; $R_4$ represents 4-tetrahydropyranyl; $R_6$ and $R_7$ represent methyl; alk represents methylene or ethylene; and $COOR_2$ represents carboxyl or lower alkoxycarbonyl; or a pharmaceutically acceptable salt thereof.

10. A compound according to claim 2 of formula Ia wherein R and $R_6$ represent hydrogen; $R_1$ represents phenyl wich is unsubstituted or substituted by phenyl or $C_1$–$C_4$ alkoxy; or $R_1$ represents indolyl or pyridyl substituted by thienyl; $R_2$ represents hydrogen or $C_1$–$C_4$ alkyl; $R_3$ represents hydrogen or $C_2$–$C_5$ alkanoyl; $R_4$ represents tetrahydropyranyl or 4-tetrahydropyranylmethyl; $R_6$ and $R_7$ represent $C_1$–$C_4$ alkyl; or $R_6$ and $R_7$, together with the carbon atom to which they are attached, represent cyclopentylidene; alk represents $C_1$ to $C_2$ alkylene; or a pharmaceutically acceptable salt thereof.

11. A compound according to claim 2 of formula Ia wherein R and $R_5$ represent hydrogen; $R_1$ represents phenyl, fluorophenyl, methoxyphenyl, 4-biphenylyl, 2-thienyl-5-pyridyl, or 3-indolyl; $R_3$ represents hydrogen or lower alkanoyl; $R_4$ represents 4-tetrahydropyranyl; $R_6$ and $R_7$ represent methyl; alk represents methylene or ethylene; and $COOR_2$ represents carboxyl or lower alkoxycarbonyl; or a pharmaceutically acceptable salt thereof.

12. A compound according to claim 2 being N-[2-[(S)-2-acetylthio-2-(4-tetrahydropyranyl)-acetylamino]-2-methyl-propionyl]-(L)-4-methoxyphenylalanine ethyl ester, N-[2-[(S)-2-mercapto-2-(4-tetrahydropyranyl)-acetylamino]-2-methylpropionyl]-(L)-4-methoxyphenylalanine, or a pharmaceutically acceptable salt thereof.

13. A compound of formula VI

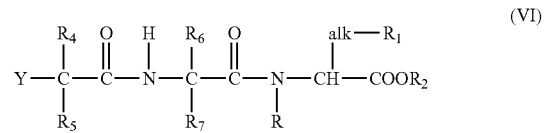

wherein R represents hydrogen, lower alkyl, carbocyclic or heterocyclic aryl-lower alkyl or cycloalkyl-lower alkyl;

$R_1$ represents hydrogen, cycloalkyl, carbocyclic or heterocyclic aryl, or biaryl; alk represents lower alkylene;

$R_4$ represents oxacycloalkyl, (thia-, oxothia- or dioxothia)-cycloalkyl, azacycloalkyl, or oxacycloalkyl-, (thia-, oxothia- or dioxothia)-cycloalkyl- or azacycloalkyl-lower alkyl;

$R_5$ represents hydrogen or lower alkyl;

$R_6$ represents lower alkyl, carbocyclic or heterocyclic aryl, (carbocyclic or heterocyclic aryl)-lower alkyl, cycloalkyl, cycloalkyl-lower alkyl, biaryl or biaryl-lower alkyl;

$R_7$ represents lower alkyl, (carbocyclic or heterocyclic aryl)-lower alkyl, cycloalkyl-lower alkyl or biaryl-lower alkyl; or $R_6$ and $R_7$, together with the carbon atom to which they are attached, represent 3- to 10-membered cycloalkylidene which may be substituted by lower alkyl or aryl-lower alkyl or may be fused to a saturated or unsaturated carbocyclic 5- to 7-membered ring; or 5- or 6-membered (oxacycloalkylidene, thiacycloalkylidene or azacycloalkylidene), each optionally substituted by lower alkyl or aryl-lower alkyl; or 2,2-norbonylidene;

$COOR_2$ represents carboxyl or carboxyl derivatized in form of a pharmaceutically acceptable ester; and Y represents a reactive esterified hydroxyl group, chloro or bromo, iodo or sulfonyloxy as a leaving group.

14. A method of inhibiting angiotensin converting enzyme and neutral endopeptidase in mammals which comprises administering to a mammal in need thereof an effective amount of a compound according to claim 1.

15. A method according to claim 14 comprising the inhibition of endothelin converting enzyme.

16. A pharmaceutical composition comprising an effective amount of a compound of claim 1 in combination with one or more pharmaceutically acceptable carriers.

17. A pharmaceutical composition according to claim 16 for inhibiting angiotensin converting enzyme and neutral endopeptidase.

18. A pharmaceutical composition according to claim 16 for inhibiting endothelin converting enzyme.

19. A pharmaceutical composition according to claim 16 further comprising at least one compound selected from the group consisting of angiotensin II receptor antagonists, renin inhibitors, calcium channel blockers, aldosterone synthase inhibitors/aldosterone antagonists, diuretics, vasopressin receptor antagonists, cardiotonic drugs, endothelin antagonists, ECE inhibitors, anti-atherosclerotic agents, cholesterol absorption inhibitors, fibrates, statins, thyromimetic agents and antidiabetic agents.

* * * * *